United States Patent [19]

Plueddemann

[11] Patent Number: 4,871,788

[45] Date of Patent: Oct. 3, 1989

[54] INOMERIC COUPLING AGENTS BASED ON AMIC ACID-FUNCTIONAL SILANES

[75] Inventor: Edwin P. Plueddemann, Midland, Mich.

[73] Assignee: Dow Corning Corporation, Midland, Mich.

[21] Appl. No.: 202,164

[22] Filed: Jun. 3, 1988

[51] Int. Cl.$^4$ .............................................. C08K 9/06
[52] U.S. Cl. .................................. 523/213; 523/216; 525/100; 525/102; 525/105; 525/431; 525/446; 556/401; 556/419; 556/134; 106/287.11; 106/287.1
[58] Field of Search ................... 106/287.11, 287.1; 556/419, 134, 401; 525/100, 102, 105, 431, 446; 528/25, 26; 523/216, 217

[56] References Cited

U.S. PATENT DOCUMENTS

| Re. 32,250 | 9/1986 | Plueddemann | 556/401 |
|---|---|---|---|
| 3,179,612 | 4/1965 | Plueddemann | 525/479 |
| 3,258,477 | 6/1966 | Plueddemann | 556/416 |
| 3,306,800 | 2/1967 | Plueddemann | 525/100 |
| 3,630,827 | 12/1971 | Hartlein | 428/392 |
| 3,734,763 | 5/1973 | Plueddemann | 556/419 |
| 3,816,235 | 6/1974 | Lin | 525/100 |
| 3,819,675 | 6/1974 | Plueddemann | 528/23 |
| 3,837,876 | 9/1974 | Mayuzumi | 106/287.11 |
| 3,884,886 | 5/1975 | Plueddemann | 528/38 |
| 3,955,036 | 5/1976 | Plueddemann | 525/102 |
| 3,956,353 | 5/1976 | Plueddemann | 556/419 |
| 3,981,851 | 9/1976 | Plueddemann | 525/102 |
| 4,001,154 | 1/1977 | Schmidt | 525/102 |
| 4,348,311 | 9/1982 | Machurst | 525/105 |
| 4,413,085 | 11/1983 | Temple | 524/321 |
| 4,690,959 | 9/1987 | Plueddemann | 523/213 |
| 4,718,944 | 1/1988 | Plueddemann | 106/287.11 |

Primary Examiner—John C. Bleutge
Assistant Examiner—Ralph H. Dean, Jr.
Attorney, Agent, or Firm—Alexander Weitz

[57] ABSTRACT

Novel ionomeric silane coupling agents are disclosed and their use in bonding a matrix polymer to a mineral substrate is described. The coupling agents comprise amic acid-functional silanes which are partially neutralized with metal cations and are prepared by reacting a mixture of (I) an amine-functional silane, (II) a stoichiometric excess of a dicarboxylic organic acid and (III) an ionic compound containing a metal cation, wherein 10% to 80% of the excess carboxylic acid functionality is neutralized by the metal cations. The coupling agents greatly improve bonding to the matrix polymer in moist environments and are particularly suitable for use in formulating filled injection molding compositions.

23 Claims, No Drawings

INOMERIC COUPLING AGENTS BASED ON AMIC ACID-FUNCTIONAL SILANES

This invention relates to the field of silane coupling agents. More specifically, this invention relates to an ionomeric silane coupling agent based on amic acid-functional silanes which are partially neutralized with metal cations. It further relates to a process of using the ionomeric silane as a coupling agent to promote bonding between a thermoplastic matrix polymer and a mineral or metal substrate.

BACKGROUND OF THE INVENTION

Silane coupling agents have been known to improve the mechanical properties of filled thermoseting and thermoplastic resins since the late 1940's. These low molecular weight compounds are believed to form chemical links between filler particles and polymer molecules, and as such, they must incorporate functional groups capable of reacting, or at least associating, with filler and resin alike.

Although use of various silanes known in the art does greatly promote adhesion between thermoplastic polymers and substrates such as mineral fillers, exposure of these composites to water does somewhat limit retention of the improved adhesion. Thus, for example, a moist environment can induces a gradual deterioration of the flexural strength of composites filled with silane-treated reinforcing fibers, and there is still need for improvement. Furthermore, when such fiber filled polymers are subjected to high shear rates, as in an injection molding operation, there is a tendency to destroy some of the covalent bonding (or any associative structure) formed between the coupling agent and the polymer. This also detracts from ultimate physical properties of the composite. There is thus a need for a coupling agent which forms strong bonds or associations between itself and the polymer under ordinary conditions, which bonds become highly mobile at the elevated temperatures encountered during injection molding. Even more desirable would be the availability of such a silane coupling agent which additionally impart bond durability when challenged by conditions of high moisture.

In a copending application, Serial No. 202,163, filed June 3, 1988, it is shown that the above mentioned desirable features can be achieved by treating a mineral substrate with an ionomeric silane composition comprising a mixture of an acid-functional silane and an acid-functional film former in which at least some of the combined acid functionality has been neutralized by the metal cation of an ionic compound. In this application, it was believed that one end of the acid-functional silane forms covalent bonds on the surface of the mineral substrate, as in the case of current art coupling agents. However, contrary to known systems, the other end of the silane is reversibly bound to the acid-functional film former through ionic interactions. It is thus hypothesized that the microscopic interphase region between the substrate and the polymer remains tough and immobile at ordinary temperatures, but is relatively fluid at the elevated temperatures and high shear rates experienced during injection molding.

SUMMARY OF THE INVENTION

It has now been further found that ionomeric silane coupling agents, similar to those described in the above cited copending application, may comprise partially neutralized metal salts of silane amic acids (i.e., those having both amide and carboxylic acid groups in the same molecule). The present invention therefore relates to an ionomeric silane coupling agent prepared by reacting (I) an amine-functional silane represented by the formula

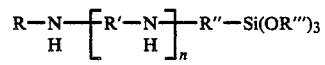

wherein R is selected from the group consisting of hydrogen and an alkyl radical having 1–4 carbon atoms, R' is a divalent hydrocarbon radical having 2 to 4 carbon atoms, R" is a divalent hydrocarbon radical having 3 to 6 carbon atoms, R''' is selected from the group consisting of methyl, ethyl and propyl radicals, and n is 0, 1 or 2;

(II) from about 1.1 to 1.5 equivalents of a dicarboxylic organic acid having 4 to 36 carbon atoms for each equivalent of reactive hydrogen atom of said amine-functional silane (I) so as to result in a stoichiometric excess of carboxylic acid functionality; and (III) a sufficient amount of an ionic compound, having a cation selected from the group consisting of monovalent and divalent metal ions, to neutralize from about 10% to 80% of said excess carboxylic acid functionality on a molar equivalent basis.

This invention also relates to a process for bonding a thermoplastic matrix polymer, selected from the group consisting of unmodified thermoplastic polymers, unmodified thermoplastic copolymers, acid-modified thermoplastic polymers, acid-modified thermoplastic copolymers and ionomeric polymers, to a substrate comprising:

(a) treating said substrate with the above described ionomeric silane coupling agent; and (b) fusing said thermoplastic matrix polymer to the treated substrate resulting from step (a).

DETAILED DESCRIPTION OF THE INVENTION

The ionomeric silane coupling agent compositions of the present invention comprise (I) an amine-functional silane and a stoichiometric excess of (II) a dicarboxylic organic acid wherein the residual acid functionality is at least partially neutralized with (III) an ionic compound having a metal cation.

The amine-functional silane (I) may be represented by the general formula

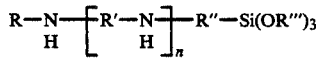

wherein R is selected from the group consisting of hydrogen and an alkyl radical having 1–4 carbon atoms and R' is a divalent hydrocarbon radical having 2 to 4 carbon atoms, preferably a dimethylene group. In the above formula, R" is a divalent hydrocarbon radical having 3 to 6 carbon atoms, preferably a trimethylene group R''' is selected from the group consisting of methyl, ethyl and propyl radicals, preferably methyl, and n is 0 1 or 2, preferably one. For the purposes of the present invention, the reactive hydrogens of the amine-functional silane which react with the dicarboxylic organic acid, described infra, are those explicity shown above. The skilled artisan will thus recognize that, once these hydrogens have reacted to form amide groups, no further reaction of a second terminal hydrogen on nitrogen would be expected (i.e., when R is hydrogen).

Examples of amine-functional silanes suitable for use as component (I) include compounds represented by the following formulas:

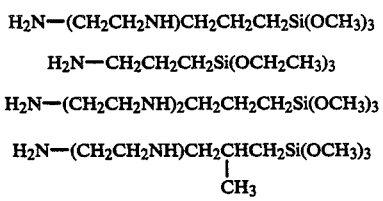

$H_2N-(CH_2CH_2NH)CH_2CH_2CH_2Si(OCH_3)_3$ (i)

$H_2N-CH_2CH_2CH_2Si(OCH_2CH_3)_3$ (ii)

$H_2N-(CH_2CH_2NH)_2CH_2CH_2CH_2Si(OCH_3)_3$ (iii)

$H_2N-(CH_2CH_2NH)CH_2\underset{\underset{CH_3}{|}}{C}HCH_2Si(OCH_3)_3$ (iv)

The amine-functional silanes are well known in the art and are typically formed by reacting chloroalkylalkoxysilanes with organic amines. The resulting amine-functional silanes are generally not pure species and several side products coexist with the main components. The amine-functional silanes of formula (i), above, is available commercially as DOW CORNING Z-6020 (Dow Corning Corp., Midland, Mich.). For the purposes of this invention, either the crude reaction products or purified components may be employed, distilled N-beta-aminoethyl-gamma-aminopropyltrimethoxyisilane (formula i, above) being preferred.

The dicarboxylic organic acid (II) contains between 4 and 36 carbon atoms, preferably 4 to 8 carbon atoms, and is exemplified by such acids as isophthalic, adipic, fumaric, succinic, sebasic maleic and commercial compounds, such as the dimer of oleic acid. It is preferred that the dicarboxylic acid be selected from aromatic acids in light of their superior thermal stability, isophthalic acid being highly preferred.

The ionic compound (III) is selected from salts, hydroxides or oxides of monovalent or divalent metals. When a metal salt is used, it is preferred that it be a water-soluble organic salt, such as an acetate or formate. Halide salts are considered unsuitable herein, however. Examples of suitable ionic compounds include those having sodium, lithium, zinc, calcium, magnesium or potassium cations. A preferred ionic compound is zinc acetate.

In order to prepare the ionomeric silane coupling agent compositions of the present invention, components (I), (II) and (III) are mixed in water or an organic solvent. It is preferred, however, that mixing be carried out in a water dispersion, from which the composition may be applied to a substrate, as described infra. In general, the ionomeric silanes of the present invention are readily dispersed in water but methods which may also be employed to disperse silane coupling agents are described by Plueddemann in U.S. Pat. No. 3,258,477. Component (II) is added in excess such that from about 1.1 to 1.5 equivalents of carboxylic functionality is available for each equivalent of reactive hydrogen of component (I). The amount of component (III) is employed at a level such that about 10% to 80% of the excess carboxylic acid functionality is neutralized by the metal cation supplied thereby (on a molar equivalent basis). Those skilled in the art will readily determine the optimum degree of neutralization required for a particular system through routine experimentation. Preferably, from about 30% to 60% the excess acid functionality is neutralized by the metal ion. The dispersion so formed contains a salt of the amine-functional silane and metal ions. This dispersion is applied to a substrate, as described infra, dried and then reacted by heating at about 150° to 200° C., whereupon the amine salt is converted to an amide, yielding amic acids (i.e., acids having amide as well as carboxylic acid functionality in the same molecule) which are partially neutralized by the metal cation.

Organic solvents suitable for dispersing the components of the present invention are the highly polar alcohols, such as ethanol, isopropanol, glycol monoethers, methanol and propylene glycol monomethyl ether, the latter two being preferred.

The compositions of the present invention may also be combined with (IV) an acid-functional film former selected from carboxylated thermoplastic polymers or carboxylated thermoplastic copolymers which are available, or can be made, in aqueous or solvent dispersion form. These materials, many of which are available commercially, are well known in the art. They are typically formed by copolymerizing a minor portion (usually no more than about 10 mole percent) of a carboxy-functional monomer with one or more reactive monomers so as to leave pendant or terminal —COOH groups on the resulting polymer or copolymer. hey may also be formed by grafting carboxylic acid functionality onto a polymer chain. In general, such carboxylated systems are the result of addition-type polymerizations, typically free radical polymerizations, but may also be based on carboxylated condensation polymers such as polyurethanes, polyesters, polyamides and alkyd resins. Selection of the film former (IV) is made on the basis of its compatibility with a thermoplastic matrix polymers, according to the process of the present invention, described infra, wherein the matrix polymer is bonded to a substrate. When such an acid-functional film former is used, the carboxylic acid functionality thereon must also be partially neutralized, as required in the case of the ionomeric silane compositions of the present invention.

A preferred film former of the present invention is a metal salt of an organic amic acid prepared by reacting one mole of an organic diamine having from 6 to 10 carbon atoms with a stoichiometric excess, preferably from about 1.1 to 1.5 moles, of a dicarboxylic acid of the present invention (II) and partially neutralizing the resulting excess carboxylic acid functionality with an ionic compound of the present invention (III), in a manner similar to the formation of the ionomeric silane coupling agents described above.

A highly preferred embodiment of the present invention results when 0.9 mole of N-beta-aminoethyl-gamma-aminopropyltrimethoxyisilane is combined with 1.0 mole of isophthalic acid and 0.02 mole of zinc acetate, the mixture then being diluted with water to a solution weight of 1000 grams. This solution remains stable during storage at room temperature. After application to a substrate, it is dried and preferably reacted at about 175° C. for about 15 minutes.

The above preferred embodiment is further advantageously combined, in various proportion, with an oligomeric polyamide film former prepared by reacting 0.9 mole of hexamethylenediamine, with 1.0 mole of adipic acid, and 0.02 mole of zinc acetate. Again, such a film former is prepared as a water soltuion and is readily mixed with the above preferred ionomeric silane solution. This solution is also stable with respect to storage at room temperature.

The present invention also relates to a process for bonding a thermoplastic matrix polymer to a substrate by (a) treating the substrate with a composition of the present invention and (b) fusing the thermoplastic matrix polymer to the treated substrate resulting from step (a).

In a first embodiment of the process of the present invention, the matrix polymer is selected from thermoplastic polymers or copolymers such as polyethylene, nylon, styrenebutadiene copolymers, olefin copolymers, polyesters and urethanes.

As alluded to above, the choice of a given matrix polymer or copolymer dictates the type of acid-functional film former (IV) which may used in the coupling agent composition, insomuch as these two materials must be compatible (i.e., they do not phase separate). Thus, for example, when the matrix polymer is polyethylene, the film former is preferably a carboxylated polyethylene. Likewise, when the matrix polymer is a polyamide, such as a nylon, the film former is preferably an oligomeric polyamide having residual carboxyl functionality.

In the above process, a substrate is first treated with one of the previously described compositions of the present invention according to methods well established in the art. The ionomeric silane coupling agent may be added from an alcohol or water dispersion or solution by dipping, spraying or a dry blending method, such as tumbling with a mineral filler in a container, or by mechanical mixing with a filler, followed by drying in air at about 175° C. Preferably, the ionomeric silane coupling agent is deposited onto the surface of the substrate from a water dispersion or solution, dried and reacted by heating, as described above.

The treated substrate may then be bonded to the matrix polymer by fusing the latter onto the former at a temperature sufficient to impart fluidity to the polymer (e.g., above the melt point in the case of a crystalline polymer).

Substrates contemplated herein can be fillers which are typically used to extend or reinforce the above mentioned thermoplastic matrix polymers. They are inorganic materials which may be of natural or synthetic origin, but have a common feature in that their surfaces contain hydroxyl functionality to a greater or lesser extent. Notable within this general category of fillers are the siliceous materials such as glass fiber, precipitated silica, ground quartz, aluminum silicate, zirconium silicate, calcium silicate, glass micro beads, mica, asbestos, clay, vitreous enamels and ceramics. Other examples of suitable fillers include alumina, silicon carbide, silicon whiskers, metals and metal oxides.

In addition to the treated fillers, which are dispersed in the matrix polymer by methods well known in the art, other components, such as catalysts, pigments, stabilizers and antioxidants may be included in a typical filler polymer formulation. These formulations may be molded into desired shapes by, e.g., compression or injection molding. As noted above, the coupling agents of the present invention are of particular advantage in treating reinforcing fillers, such as glass fibers, for use in compositions for injection molding.

The substrate may also consist of a bulk material, wherein the coupling agents of the present invention are used to prime the surfaces thereof. Examples of such substrates include glass, mica composites, asbestos composites, fired clay, vitreous enamel, silicon carbide, alumina and ceramics, inter alia. Methods for using silane coupling agents as primers are well known in the art. Typically, the surface of a substrate is wetted by the coupling agent by dipping, brushing, spraying, or wiping, for example. As before, the silane may be applied from solution or dispersion, the preferred method being application from aqueous solution or dispersion at about a 5 to 20% (by weight) concentration. After application, the primed surface is usually dried to remove any solvent or water employed and is then baked at 150° to 175° C. to yield the amic acid salts. The primed surface of this invention forms water-resistant bonds to the matrix polymer when it is fused thereto.

In a second embodiment of the process of the present invention, the matrix polymer is selected from thermoplastic acid-modified polymers or copolymers. These materials are also well known in the art and are substantially identical to the matrix polymers described above wherein a minor portion of acid functionality has been copolymerized into the main polymer chain or grafted thereto. Thus, the carboxylated polymer dispersions used as component (IV), supra, form one class of such acid-modified systems. In this case, however, they may also take the form of bulk polymers.

Additionally, the acid-modified polymer may be an ionomer. In this case, the ionic content of the polymer should be taken into account in determining the proper degree of neutralization of the acid functionality of component (II) of the present invention.

In the second embodiment of the process of the present invention, it is further contemplated that a minor portion (e.g., from about 1 to 10 weight percent) of an acid-modified polymer may be blended with a compatible unmodified matrix polymer.

It has also been found that, when the matrix polymer is selected from acid-modified polymers, the above mentioned blend of acid-modified polymer and unmodified polymer or an ionomeric polymer, the need for the acid-functional film former of the present invention is reduced or completely eliminated. In any event, the principle of partial neutralization, outlined above, again applies.

EXAMPLES

The following examples are offered for the purpose of illustration and should not be construed as limiting the claimed invention.

Materials used in the examples included:

Z-6020 (Dow Corning Corp., Midland, Mich.) is an amine-functional silane consisting essentially of N-beta-aminoethyl-gamma-aminopropyltrimethoxyisilane.

PLEXAR-6 is described as a carboxylated polyethylene (Chemplex Co., Rolling Meadows, Ill.).

PRIMACOR 4983 is described as an aqueous emulsion of a polyethylene-acrylic acid copolymer (Dow Chemical Co., Midland, Mich.).

PRIMACOR 3960 is described as an acid-modified polyethylene having a melt index of 20 and an acrylic acid content of 9.7 mole percent (Dow Chemical Co., Midland, Mich.).

ACLYN 295 is described as a low molecular weight ionomer (Allied Signal, Inc., Morristown, N.J.).

EMPOL 1024 is described as a dicarboxylic acid consisting essentially of the dimer of oleic acid. (Emery Industries, Cincinnati, Ohio).

Z-6032 is a 40% by weight solution in methanol of N-beta-(N-vinylbenzylamino)ethyl-gamma-aminopropyl trimethoxysilane monohydrogen chloride (Dow Corning Corp., Midland, Mich.).

DL 638A is described as an acid-modified styrene-butadiene latex (Dow Chemical Co., Midland, Mich.).

RUCOTHANE is described as a carboxylic acid-modified urethane latex (Ruco Polymer Corp., Hicksville, N.Y.).

Primer dispersions of the present invention were prepared by mixing the indicated molar quantities of the various ingredients and diluting the mixtures in water.

The primer dispersions were applied to pre-cleaned glass microscope slides by wiping with a paper tissue and allowing the coatings to dry and bake at the indicated temperatures. Initial adhesion of the acid-modified polymer to the glass surface was determined by prying or scraping the films from the glass slides using a razor blade. The slides were then submerged in water at room temperature and the adhesion of the polymer to the primed glass was monitored using the following rating scheme:

| Rating | Observation |
| --- | --- |
| nil | Fell off (Dry) or Floated free of glass slide (Wet) (adhesive failure). |
| fair | Could be removed in one piece with razor blade (adhesive failure). |
| good | Could be pried off in pieces (adhesive and cohesive failure). |
| excellent | Could not be removed from glass (cohesive failure). |

Time to failure is defined as the point at which the adhesion rating dropped below "good" or fell off completely.

EXAMPLES 1-3

A primer composition of the present invention (SILANE A), containing 1 mole of Z-6020, 1.1 moles of isophthalic acid and sufficient zinc acetate to neutralize 40% of the excess carboxylic acid functionality was applied from water to a microscope slide, as described above. After the coatings had dried, a thin film (approximately 10 mils thick) of PRIMACOR 3960 was fused onto the primed slide surface by pressing at 200° C. (Example 2).

In a similar manner, a primed slide was fused with a polyethylene composition which was blended with 5 weight percent of PRIMACOR 3960 (Example 3).

(Comparative) Example 1, in which the slide was not primed was also fused with the PRIMACOR 3960 and served as a control. Adhesion results, according to the above described test method, are reported in Table 1.

TABLE 1

| Sample | Initial Adhesion Rating (Dry) | Time to Failure (Wet) |
| --- | --- | --- |
| (Comparative) Example 1 | excellent | 2 hours |
| Example 2 | excellent | >10 days |
| Example 3 | excellent | >2 days |

EXAMPLES 4-5

The above primer composition (SILANE A) was applied to a glass slide as before. An acid-functional emulsion, PRIMACOR 4983, was coated over the primed surface after it had dried and the combination was baked at 175° C. for about 15 minutes (Example 5).

(Comparative) Example 4 was similarly prepared, but the slide was not primed. Adhesion test results are presented in Table 2.

TABLE 2

| Sample | Initial Adhesion Rating (Dry) | Time to Failure (Wet) |
| --- | --- | --- |
| (Comparative) Example 4 | excellent | 4 hours |
| Example 5 | excellent | >14 days |

EXAMPLES 6-8

A one molal solution of the primer composition used in Example 2 was mixed with an equal weight of the PRIMACOR 4983 emulsion (i.e., film former) and applied to a glass slide, as above. This coating was dried for 15 minutes at 100° C. and a thin film of high density polyethylene was fused onto the slide at 250° C. (Example 8). Adhesion test results appear in Table 3.

(Comparative) Example 6 shows a control slide which was fused to the polyethylene without benefit of either primer of the PRIMACOR 4983.

(Comparative) Example 7 shows a control slide which was not primed with the SILANE A but was coated with the PRIMACOR 4983 emulsion.

TABLE 3

| Sample | Initial Adhesion Rating (Dry) | Time to Failure (Wet) |
| --- | --- | --- |
| (Comparative) Example 6 | poor | 1 hour (nil rating) |
| (Comparative) Example 7 | excellent | 2 hours (poor) |
| Example 8 | excellent | >10 days (exc.) |

EXAMPLES 9-18

One tenth of a mole of isophthalic acid was mixed with 0.09 mole of Z-6020 and diluted with water to 100 grams of solution (SILANE B).

Likewise, 0.1 mole of adipic acid and 0.09 mole of hexamethylenediamine was diluted to 100 grams in water (OLIGOMER A).

Equal weights of these two solutions were mixed and partially neutralized with various metal acetates to form primer compositions. These primers were applied to slides, as before, and baked for 15 minutes at 175° C. Thin films of nylon 6,6 were fused to the primed surfaces at 250° C. Initial adhesion of the films was good in all cases and the slides were then soaked in 95° C. water and were periodically evaluated for retention of adhesion, as indicated in Table 4. In this table, the amount of the metal acetate used in each sample is presented in terms of the percentage of calculated excess carboxylic acid functionality neutralized in the primer composition.

TABLE 4

| Sample | Metal Ion | Percent Neutralization | Adhesion Rating | | |
| --- | --- | --- | --- | --- | --- |
| | | | 2 hours | 4 hours | 6 hours |
| (Comparative) Example 9 | — | No Primer | poor | — | — |
| (Comparative) Example 10 | — | 0 | exc. | good | poor |
| (Comparative) Example 11 | $Zn^{++}$ | 100 | exc. | good | poor |
| (Comparative) Example 12 | $Mg^{++}$ | 60 | good | fair | poor |
| (Comparative) Example 13 | $Na^{+}$ | 10 | exc. | good | poor |

TABLE 4-continued

| Sample | Metal Ion | Percent Neutralization | Adhesion Rating 2 hours | 4 hours | 6 hours |
|---|---|---|---|---|---|
| Example 14 | $Zn^{++}$ | 20 | exc. | exc. | fair |
| Example 15 | $Zn^{++}$ | 40 | exc. | exc. | exc. |
| Example 16 | $Zn^{++}$ | 60 | exc. | exc. | good |
| Example 17 | $Ca^{++}$ | 60 | good | fair | fair |
| Example 18 | $Na^{+}$ | 30 | exc. | exc. | good |

From Table 4 it can be seen that 100% neutralization with zinc ions was too much, while 10% neutralization with sodium ions and 60% neutralization with Magnesium, was not adequate in this nylon 6,6 polymer. This illustrates the need for optimization of each combination of polymer and ionomeric silane coupling agent through routine experimentation.

EXAMPLES 19–22

Primer compositions were prepared and tested according to the methods of Examples 9–18 wherein different acids were substituted for the isophthalic acid in the mixture with the Z-6020, as indicated in Table 5. In these primers, 40% of the excess carboxylic acid functionality was neutralized using zinc acetate.

TABLE 5

| Sample | Dicarboxylic Acid Used in Primer | Adhesion Rating 2 hours | 4 hours | 6 hours |
|---|---|---|---|---|
| (Comparative) Example 19 | Malonic | fair | poor | — |
| Example 20 | Adipic | exc. | exc. | fair |
| Example 21 | Fumaric | exc. | exc. | fair |
| Example 22 | EMPOL 1024 | exc. | exc. | exc. |

Examples 23–33

Compositions of the present invention, prepared according to the methods of Examples 9–18, were used to treat glass cloth by dipping the cloth in a 1 weight percent aqueous solution and drying at 175° C. for 15 minutes. Six layers of the primed glass cloth were fused with seven alternating layers of nylon 6,6 at 250° C. to form ¼ inch thick fiberglass laminates.

The resulting laminates were cut into ½ inch wide strips which were tested for flexural strength, dry and after soaking for 2 hours in boiling water. Table 6 presents results for systems with equal weight of film former OLIGOMER A, as well as for the case where only a silane of the present invention was used. In Table 6, SILANE C is the same as SILANE B wherein the isophthalic acid was replaced by adipic acid.

EXAMPLES 34–36

A primer composition of the present invention (SILANE D), containing 1 mole of Z-6020, 1.1 moles of isophthalic acid and sufficient zinc acetate to neutralize 50% of the excess carboxylic acid functionality was applied from water to a microscope slide, as described above. After the coating had dried, a thin film of ACLYN 295 was fused onto the primed slide surface by pressing at 155° C. (Example 36).

In a similar manner, (Comparative) Example 35 was prepared and fused with the ionomer film, wherein the combination of Z-6020 and the isophthalic acid of the primer was not neutralized. Additionally, in (Comparative) Example 34, the ionomer film was fused onto an unprimed slide.

The adhesion of the ionomer films was measured after the slides were soaked in room temperature water for 2 hours, the results being reported in Table 7.

TABLE 7

| Sample | Adhesion of ACLYN 295 To Slide (Newtons/cm) |
|---|---|
| (Comparative) Example 34 | nil |
| (Comparative) Example 35 | 1.1 |
| Example 36 | >5.5 (Cohesive Failure of Film) |

I claim:

1. An ionomeric silane composition prepared by reacting (I) an amine-functional silane represented by the formula

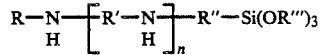

wherein R is selected from the group consisting of hydrogen and an alkyl radical having 1–4 carbon atoms, R' is a divalent hydrocarbon radical having 2 to 4 carbon atoms, R" is a divalent hydrocarbon radical having 3 to 6 carbon atoms, R''' is selected from the group consisting of methyl, ethyl and propyl radicals, and n is 0, 1 or 2;

(II) from about 1.1 to 1.5 equivalents of a dicarboxylic organic acid having 4 to 36 carbon atoms for each equivalent of reactive hydrogen atom of said amine-functional silane (I) so as to result in a stoi-

TABLE 6

| Sample | Silane | Film Former | Ion | Percent Neutralization | Flexural Strength (psi) Dry | Wet |
|---|---|---|---|---|---|---|
| (Comparative) Example 23 | None | — | — | — | 26,000 | 10,600 |
| (Comparative) Example 24 | Z-6032 | — | — | — | 34,200 | 20,500 |
| (Comparative) Example 25 | SILANE B | — | — | 0 | 25,000 | 17,700 |
| (Comparative) Example 26 | SILANE B | OLIGOMER A | — | 0 | 28,000 | 16,000 |
| Example 27 | SILANE B | — | $Zn^{++}$ | 25 | 35,000 | 27,000 |
| Example 28 | SILANE B | OLIGOMER A | $Zn^{++}$ | 40 | 29,500 | 19,200 |
| Example 29 | SILANE B | OLIGOMER A | $Mg^{++}$ | 40 | 39,000 | 27,000 |
| Example 30 | SILANE B | OLIGOMER A | $Ca^{++}$ | 40 | 36,000 | 24,000 |
| Example 31 | SILANE C | OLIGOMER A | $Zn^{++}$ | 40 | 25,000 | 20,000 |
| Example 32 | SILANE C | DL 638A | $Zn^{++}$ | 40 | 25,000 | 18,000 |
| Example 33 | SILANE C | RUCOTHANE | $Zn^{++}$ | 40 | 20,000 | 13,000 | chiometric excess of carboxylic acid functionality; and (III) a sufficient amount of an ionic compound, having a cation selected from the group consisting of monovalent and divalent metal ions, to neutralize from about 10% to 80% of said excess carboxylic acid functionality on a molar equivalent basis.

2. A composition according to claim 1, wherein component (II) is selected from the group consisting of dicarboxylic organic acids having from 4 to 8 carbon atoms.

3. A composition according to claim 2, wherein the metal cation of said ionic compound (III) is selected from the group consisting of sodium, zinc, lithium, calcium, magnesium and potassium ions.

4. A composition according to claim 3, wherein R''' of said amine-functional silane (I) is a methyl radical.

5. A composition according to claim 4, wherein R of said amine-functional silane (I) is hydrogen.

6. A composition according to claim 5, wherein said dicarboxylic organic acid is isophthalic acid and the metal cation of said ionic compound is selected from the group consisting of sodium and zinc ions.

7. A composition according to claim 6, wherein said amine-functional silane (I) is N-beta-aminoethyl-gamma-aminopropyltrimethoxyisilane.

8. A composition according to claim 1, further comprising (IV) an acid-functional film former selected from the group consisting of carboxylated thermoplastic homopolymers and carboxylated thermoplastic copolymers.

9. A composition according to claim 1, further comprising a film former prepared by reacting an organic diamine having from 6 to 10 carbon atoms, a stoichiometric excess of a dicarboxylic acid having 4 to 36 carbon atoms and a sufficient amount of an ionic compound, having a cation selected from the group consisting of monovalent and divalent metal ions, to neutralize from about 10% to 80% of said excess carboxylic acid functionality on a molar equivalent basis.

10. A composition according to claim 9, wherein said amine-functional silane (I) is N-beta-aminoethyl-gamma-aminopropyltrimethoxyisilane, said dicarboxylic organic acid (II) is isophthalic acid, said metal cation (III) is zinc ion and said film former is a reaction product of hexamethylenediamine, adipic acid and an ionic compound having a zinc cation.

11. A composition comprising:

(I) an amine-functional silane represented by the formula

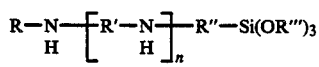

wherein R is selected from the group consisting of hydrogen and an alkyl radical having 1–4 carbon atoms, R' is a divalent hydrocarbon radical having 2 to 4 carbon atoms, R'' is a divalent hydrocarbon radical having 3 to 6 carbon atoms, R''' is selected from the group consisting of methyl, ethyl and propyl radicals, and n is 0, 1 or 2;

(II) from about 1.1 to 1.5 equivalents of a dicarboxylic organic acid having 4 to 36 carbon atoms for each equivalent of reactive hydrogen atom of said amine-functional silane (I) so as to result in a stoichiometric excess of carboxylic acid functionality; and (III) a sufficient amount of an ionic compound, having a cation selected from the group consisting of monovalent and divalent metal ions, to neutralize from about 10% to 80% of said excess carboxylic acid functionality on a molar equivalent basis.

12. A composition according to claim 11, wherein component (II) is selected from the group consisting of dicarboxylic organic acids having from 4 to 8 carbon atoms.

13. A composition according to claim 12, wherein the metal cation of said ionic compound (III) is selected from the group consisting of sodium, zinc, lithium, calcium, magnesium and potassium ions.

14. A composition according to claim 13, wherein R''' of said amine-functional silane (I) is a methyl radical.

15. A composition according to claim 14, wherein R of said amine-functional silane (I) is hydrogen.

16. A composition according to claim 15, wherein said dicarboxylic organic acid is isophthalic acid and the metal cation of said ionic compound is selected from the group consisting of sodium and zinc ions.

17. A composition according to claim 16, wherein said amine-functional silane (I) is N-beta-aminoethyl-gamma-aminopropyltrimethoxyisilane.

18. A composition according to claim 11, further comprising (IV) an acid-functional film former selected from the group consisting of carboxylated thermoplastic homopolymers carboxylated thermoplastic copolymers.

19. A composition according to claim 11, further comprising a film former consisting essentially of an organic diamine having from 6 to 10 carbon atoms, a stoichiometric excess of a dicarboxylic acid having 4 to 36 carbon atoms and a sufficient amount of an ionic compound, having a cation selected from the group consisting of monovalent and divalent metal ions, to neutralize from about 10% to 80% of said excess carboxylic acid functionality on a molar equivalent basis.

20. A composition according to claim 19, wherein said amine-functional silane (I) is N-beta-aminoethyl-gamma-aminopropyltrimethoxyisilane, said dicarboxylic organic acid (II) is isophthalic acid, said metal cation (III) is zinc ion and said film former is a reaction product of hexamethylenediamine, adipic acid and an ionic compound having a zinc cation.

21. A composition according to claim 11, further comprising water as a dispersing medium.

22. In a composition suitable for injection molding comprising a thermoplastic matrix polymer and a mineral filler treated with a silane coupling agent, the improvement comprising using the composition of claim 1 as said coupling agent.

23. In a composition suitable for injection molding comprising a thermoplastic matrix polymer and a mineral filler treated with a silane coupling agent, the improvement comprising using the composition of claim 6 as said coupling agent.

* * * * *